United States Patent
Kumano et al.

(10) Patent No.: US 8,212,080 B2
(45) Date of Patent: Jul. 3, 2012

(54) PRODUCTION METHOD OF XYLYLENEDIAMINE

(75) Inventors: Tatsuyuki Kumano, Okayama (JP); Kenji Nakaya, Okayama (JP); Shinichi Nagao, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 412 days.

(21) Appl. No.: 12/633,223

(22) Filed: Dec. 8, 2009

(65) Prior Publication Data
US 2010/0168474 A1  Jul. 1, 2010

(30) Foreign Application Priority Data
Dec. 26, 2008 (JP) ................. 2008-332835

(51) Int. Cl.
*C07C 209/00* (2006.01)
*C07C 211/00* (2006.01)
(52) U.S. Cl. ............... 564/375; 564/336; 564/391
(58) Field of Classification Search .............. None
See application file for complete search history.

(56) References Cited

U.S. PATENT DOCUMENTS

| | | | |
|---|---|---|---|
| 6,476,269 B2 | 11/2002 | Nakamura et al. | |
| 7,368,610 B2 * | 5/2008 | Hugo et al. | 564/385 |
| 7,528,284 B2 * | 5/2009 | Hugo et al. | 564/415 |
| 2003/0013917 A1 | 1/2003 | Nakamura et al. | |
| 2004/0002614 A1 | 1/2004 | Amakawa et al. | |

FOREIGN PATENT DOCUMENTS

| | | |
|---|---|---|
| EP | 1 760 070 A1 | 3/2007 |
| JP | 38-8719 | 10/1960 |
| JP | 53-20969 | 6/1978 |
| JP | 2002-105035 | 4/2002 |
| JP | 2003-26639 | 1/2003 |
| JP | 2004-35427 | 2/2004 |
| JP | 2007-505067 | 3/2007 |
| JP | 2007-505068 | 3/2007 |

OTHER PUBLICATIONS

U.S. Appl. No. 13/062,334, filed Mar. 4, 2011, Nagao, et al.

* cited by examiner

*Primary Examiner* — Karl J Puttlitz
(74) *Attorney, Agent, or Firm* — Oblon, Spivak, McClelland, Maier & Neustadt, L.L.P.

(57) ABSTRACT

A method of producing xylylenediamine by the hydrogenation of dicyanobenzene obtained by the ammoxidation of xylene in a high yield while prolonging the catalyst life. In the method, a molten dicyanobenzene from which compounds having a boiling point lower than that of dicyanobenzene have been removed but compounds having a boiling point higher than that of dicyanobenzene are not removed is dissolved in a solvent containing liquid ammonia. By this dissolution, at least part of dicyanobenzene polymers precipitates as insolubles. The precipitates are removed by a solid-liquid separation. By subjecting the resulting solution containing the dicyanobenzene polymers in a reduced amount to hydrogenation, xylylenediamine is produced in a high yield and the life time of hydrogenation catalyst is prolonged.

13 Claims, 1 Drawing Sheet

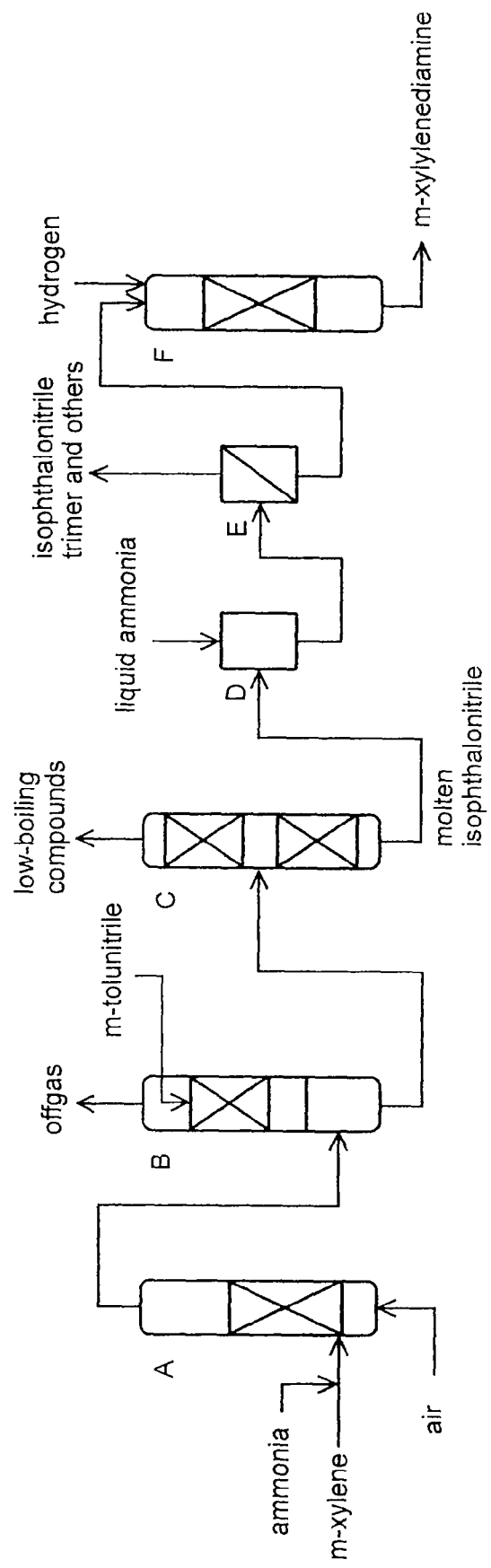

PRODUCTION METHOD OF XYLYLENEDIAMINE

BACKGROUND OF THE INVENTION

1. Field of the Invention

The present invention relates to a method of producing xylylenediamine by the hydrogenation of dicyanobenzene. Xylylenediamines are useful as the material for polyamide resins, hardeners, etc. and the intermediate material for isocyanate resins, etc.

2. Description of the Prior Art

Various methods have been proposed for the production of xylylenediamine by the liquid-phase hydrogenation of dicyanobenzene in the presence of a catalyst. For example, Patent Document 1 describes a batch-wise hydrogenation of phthalonitrile into the corresponding xylylenediamine using an autoclave in an alcohol solvent in the presence of Raney nickel or Raney cobalt together with a small amount of a caustic alkali. Patent Document 2 describes a catalytic reduction of phthalonitrile with hydrogen in liquid phase in the presence of a nickel-copper-molybdenum-containing catalyst. In the working examples, the catalytic reduction is carried out by a fixed bed continuous hydrogenation.

Patent Document 3 describes a production method of m-xylylenediamine in which impurities having a boiling point higher than that of isophthalonitrile are removed from the isophthalonitrile obtained by the ammoxidation of m-xylene in the first distillation step, the organic solvent is removed in the second distillation step, and isophthalonitrile from the column bottom is added with a specific solvent and liquid ammonia and then hydrogenated. Patent Document 4 describes a production method of xylylenediamine, which comprises contacting the ammoxidation gas of xylene directly with an organic solvent or with molten phthalonitrile, removing components having a boiling point lower than that of phthalonitrile from the resulting solution in an organic solvent, suspension or phthalonitrile melt, removing components having a boiling point higher than that of phthalonitrile before the hydrogenation.

Patent Document 5 teaches that xylylenediamine is obtained in a high yield and the catalyst life is prolonged by conducting the hydrogenation of phthalonitrile while controlling the concentration of benzamide, benzoic acid and their related compounds (impurities having a boiling point higher than that of phthalonitrile) in the hydrogenation liquid at a specific level or lower by distilling off benzamide, benzoic acid and their related compounds.

Patent Document 6 describes a production method of xylylenediamine in which the ammoxidation gas of xylene is contacted with an organic solvent and then the resulting solution is added with liquid ammonia and the hydrogenation is conducted without separating the phthalonitrile absorbed in the organic solvent. Patent Document 7 describes a production method of xylylenediamine, which comprises contacting the ammoxidation gas of xylene directly with an organic solvent or with molten phthalonitrile, removing components having a boiling point lower than that of phthalonitrile from the resulting solution in the organic solvent, suspension or phthalonitrile melt, and conducting the hydrogenation without removing the component having a boiling point of higher than that of phthalonitrile.

Patent Document 1: JP 38-8719B
Patent Document 2: JP 53-20969B
Patent Document 3: JP 2003-26639A
Patent Document 4: JP 2007-505068A
Patent Document 5: JP 2004-35427A
Patent Document 6: JP 2002-105035A
Patent Document 7: JP 2007-505067A Dicyanobenzene is produced by a known ammoxidation of dialkylbenzene such as xylene, for example, by a method described in Patent Documents 8 to 15.
Patent Document 8: JP 49-45860B
Patent Document 9: JP 49-13141A
Patent Document 10: JP 63-190646A
Patent Document 11: JP 1-275551A
Patent Document 12: JP 5-170724A
Patent Document 13: JP 9-71561A
Patent Document 14: JP 11-246506A
Patent Document 15: JP 2003-267942A

SUMMARY OF THE INVENTION

The yield of xylylenediamine in the hydrogenation of dicyanobenzene can be increased by expediting the progress of the hydrogenation of nitrile groups to aminomethyl groups, for example, by increasing the conversion of nitrile groups and increasing the selectivity of aminomethyl group. To produce xylylenediamine by the hydrogenation of dicyanobenzene efficiently for a long term, therefore, it is necessary to keep the progress of the hydrogenation high as long as possible by preventing the deactivation of the hydrogenation catalyst. The concentrations of dicyanobenzene and cyanobenzylamine in a product solution after the hydrogenation are increased as the hydrogenation catalyst is deactivated. Therefore, it is preferred to employ the reaction conditions capable of keeping the concentrations of these compounds low.

As described in Patent Documents 3 to 5, the deactivation of the hydrogenation catalyst due to the compounds having a boiling point higher than that of dicyanobenzene (hereinafter referred to as "high-boiling compounds") which are contained in dicyanobenzene may be avoided by distilling off the high-boiling compounds. However, the removal of the high-boiling compounds by distillation requires the initial cost for distillation column and the energy cost for distillation, and in addition, causes the degradation of part of dicyanobenzene due to heat polymerization during distillation, thereby making the production method economically disadvantageous. For example, in Example 1 of Patent Document 3, it is described that 2% of isophthalonitrile is degraded by heating when high-boiling compounds are removed from isophthalonitrile by distillation at a column bottom temperature of 204° C. Therefore, it has been recognized that the removal of high-boiling compounds by distillation be avoided for an economical production of dicyanobenzene.

The inventors tried to produce xylylenediamine by the hydrogenation of dicyanobenzene without removing high-boiling compounds in accordance with the method described in Patent Document 7. However, xylylenediamine is not produced stably, because the hydrogenation catalyst was deactivated in earlier stage.

Therefore, an object of the present invention is to provide a method of producing xylylenediamine by the hydrogenation of dicyanobenzene obtained by the ammoxidation of xylene, which produces xylylenediamine in a high yield stably and economically while prolonging the catalyst life.

As a result of studies on the production of xylylenediamine by the hydrogenation of dicyanobenzene, the inventors have found that the deactivation of hydrogenation catalyst is prevented by hydrogenating a starting dicyanobenzene which is reduced in the content of one of high-boiling compounds, i.e., dicyanobenzene polymers such as dicyanobenzene trimers. It has been further found that liquid ammonia, which increases the yield of xylylenediamine by preventing the side reaction in the hydrogenation of dicyanobenzene, is a poor solvent to the dicyanobenzene polymers.

On the basis of these findings, the inventors have found that part of the dicyanobenzene polymers precipitates as insolubles when a molten dicyanobenzene from which compounds having a boiling point lower than dicyanobenzene (hereinafter referred to as "low-boiling compounds") have been removed but high-boiling compounds are not removed is dissolved in a solvent containing liquid ammonia, found that the content of the dicyanobenzene polymers are reduced without degradation (polymerization) of dicyanobenzene by removing the precipitates by a solid-liquid separation, and further found that xylylenediamine is produced in a high yield by the hydrogenation of the resulting solution and the deactivation of hydrogenation catalyst is prevented.

Thus, the method of producing xylylenediamine of the present invention comprises the following steps:
(1) an ammoxidation step of ammoxidizing xylene by a vapor phase catalytic reaction with ammonia and an oxygen-containing gas in the presence of a catalyst, thereby producing an ammoxidation gas containing dicyanobenzene;
(2) an absorption step of contacting the ammoxidation gas with an organic solvent directly, thereby absorbing dicyanobenzene in the organic solvent;
(3) a removal step of low-boiling compounds wherein the dicyanobenzene-containing solution from the absorption step is distilled, to remove compounds having a boiling point lower than that of dicyanobenzene together with the organic solvent partly or completely and obtain a molten dicyanobenzene;
(4) a dissolution step of dissolving the molten dicyanobenzene from the removal step of low-boiling compounds in a liquid ammonia solvent or a mixed solvent of at least one aromatic hydrocarbon and liquid ammonia;
(5) a solid-liquid separation step of removing insolubles in the solution from the dissolution step partly or completely; and
(6) a hydrogenation step of hydrogenating dicyanobenzene in the solution from the solid-liquid separation step in liquid phase in the presence of a catalyst.

According to the present invention, xylylenediamine is produced by the hydrogenation of dicyanobenzene obtained by the ammoxidation of xylene in a high yield stably and economically while prolonging the catalyst life. Therefore, the present invention is of industrially great value.

BRIEF DESCRIPTION OF THE DRAWINGS

FIG. 1 is a process flow sheet showing an embodiment of the present invention, in which isophthalonitrile is produced by ammoxidation and then m-xylylenediamine is produced by the hydrogenation of isophthalonitrile. In FIG. 1, A is an ammoxidation reactor, B is an isophthalonitrile absorption column, C is a distillation column, D is a dissolution tank, E is a filter, and F is a hydrogenation reactor.

DETAILED DESCRIPTION OF THE INVENTION

In the present invention, dicyanobenzene collectively includes three isomers, i.e., phthalonitrile(1,2-dicyanobenzene), isophthalonitrile(1,3-dicyanobenzene), and terephthalonitrile(1,4-dicyanobenzene) and each thereof is produced by a known ammoxidation of the corresponding xylene (o-, m- or p-xylene).

Dicyanobenzene is hydrogenated to the corresponding xylylenediamine (o-, m- or p-xylylenediamine). The production method of the present invention is particularly suitable for the production of m-xylylenediamine by the hydrogenation of isophthalonitrile which is obtained by the ammoxidation of m-xylene.

The production method of the invention includes the following steps.
(1) Ammoxidation Step In this step, xylene is ammoxidized by the vapor phase catalytic reaction with ammonia and an oxygen-containing gas in the presence of a catalyst, to obtain the corresponding dicyanobenzene. The ammoxidation may be conducted in either a fluid bed manner or a fixed bed manner.

Known ammoxidation catalysts, for example, catalysts described in Patent Documents 8, 11, 12, 14, and 15 are usable. Particularly preferred are vanadium- and/or chromium-containing catalysts. The catalyst may be used in an amount used in a known ammoxidation of xylene and not particularly limited in the present invention.

The starting ammonia may be of industrial grade. The amount of ammonia to be used is preferably 2 to 20 mol and more preferably 6 to 15 mol, each based on one mole of xylene. Within the above ranges, the yield of dicyanobenzene is good and the space time yield is high. The non-reacted ammonia in the ammoxidation gas may be recovered and reused in the next ammoxidation. The non-reacted ammonia may be recovered from the ammoxidation gas by various methods, with a method of allowing the non-reacted ammonia to be absorbed by water and then removing other by-products by distillation being industrially advantageous.

Generally, air is preferably used as the oxygen-containing gas for the ammoxidation. A diluted air or oxygen with an inert gas such as nitrogen, carbon dioxide and offgas is also usable. The amount of oxygen to be used is preferably 3 mol or more, more preferably 3 to 100 mol, and still more preferably 4 to 100 mol, each based on one mole of xylene. Within the above ranges, the yield of dicyanobenzene is good and the space time yield is high.

The ammoxidation temperature is preferably 300 to 500° C. and more preferably 330 to 470° C. Within the above ranges, the conversion of xylene is good and the by-production of carbon dioxide, hydrogen cyanide, etc. is prevented, thereby enabling the production of dicyanobenzene in high yields. The ammoxidation may be conducted under ordinary pressure (atmospheric pressure), increased pressure or reduced pressure, and preferably under ordinary pressure to 300 kPa. The space velocity (GHSV: gas hourly space velocity) of the raw materials is preferably 500 to 5000 $h^{-1}$.
(2) Absorption Step In the present invention, the ammoxidation gas from the ammoxidation reactor is brought into direct contact with an organic solvent, thereby allowing the dicyanobenzene to be absorbed into the organic solvent. The organic solvent to be used in the absorption step has a boiling point lower than that of dicyanobenzene and a relatively high dissolving power to dicyanobenzene, and is inert to dicyanobenzene. Preferred examples of the organic solvents meeting these requirements include at least one solvent selected from alkylbenzenes such as xylene (inclusive of o-, m-, and p-xylene), pseudocumene, mesitylene, and ethylbenzene; heterocyclic compounds such as methylpyridine; aromatic nitriles such as tolunitrile (inclusive of o-, m-, and p-tolunitrile) and benzonitrile; and heterocyclic nitriles such as cyanopyridine, with tolunitrile being particularly preferred. In the absorption step, the ammoxidation gas is bought into direct contact with the organic solvent preferably at 80 to 200° C. for 1 to 30 s. The amount of the organic solvent to be used is preferably 0.5 to 20 parts by weight based on one part by weight of dicyanobenzene.

(3) Removal Step of Low-Boiling Compounds

The dicyanobenzene-containing solution from the absorption step is distilled, to remove the low-boiling compound inclusive of the organic solvent partly or completely and obtain a molten dicyanobenzene. The method of distillation is not particularly limited as long as the low-boiling compound inclusive of the organic solvent is removed partly or completely and the molten dicyanobenzene is obtained. For example, when a distillation column is used, the low-boiling compound inclusive of the organic solvent is removed from the column top or both the column top and the side-cut outlet (condensed zone). The recovered solution may be reused as the organic solvent in the absorption step to absorb dicyanobenzene contained in the ammoxidation gas. The distillation using a distillation column is preferably conducted under reduced pressure (for example, a column top pressure of 1 to 30 kPa) and at a temperature where dicyanobenzene does not precipitate in a condensed zone (portion upper than the feeding point). From the bottom of the distillation column, dicyanobenzene is obtained in molten state. The column bottom temperature is preferably set at a temperature equal to or higher than the melting point of dicyanobenzene and as low as possible so as to prevent the production of dicyanobenzene polymers by heating. For example, the column bottom temperature is preferably 150 to 200° C., more preferably 150 to 180° C., and particularly preferably 150 to 170° C. if dicyanobenzene is phthalonitrile; preferably 170 to 220° C., more preferably 170 to 200° C., and particularly preferably 170 to 190° C. if dicyanobenzene is isophthalonitrile; and preferably 240 to 290° C., more preferably 240 to 270° C., and particularly preferably 240 to 260° C. if dicyanobenzene is terephthalonitrile. The residence time of the molten dicyanobenzene at the column bottom is preferably as short as possible to prevent the production of dicyanobenzene polymers (for example, within 180 min). Therefore, it is preferred to design the distillation column to have a column bottom volume as small as possible as long as the operation of the distillation column is not adversely affected.

(4) Dissolution Step

The molten dicyanobenzene from the removal step of low-boiling compounds is dissolved in a liquid ammonia solvent or a mixed solvent of at lease one aromatic hydrocarbon and liquid ammonia. The amount of the solvent to be used is preferably 1 to 99 parts by weight, more preferably 3 to 99 parts by weight, and particularly preferably 5 to 99 parts by weight, each based on one part by weight of dicyanobenzene. Since the solubility of dicyanobenzene polymers to liquid ammonia is small, a higher concentration of liquid ammonia in the mixed solution is recommended, preferably 30% by weight or more, more preferably 50% by weight or more, and particularly 80% by weight or more (each inclusive of 100% by weight). The dissolving operation may be conducted by using a line mixer. However, the inside of mixer may be clogged by the adhesion of precipitated insolubles. Therefore, the dissolving operation is preferably conducted in a separate dissolution tank under mixing for dissolution. Although the molten dicyanobenzene is dissolved in the solvent by merely feeding the molten dicyanobenzene and the solvent to the dissolution tank without particular stirring, the dissolution may be conducted under stirring if necessary. The pressure and temperature in the dissolution tank are selected so as to maintain the solvent in liquid phase. The pressure in the dissolution tank is preferably 0.5 to 15 MPa, more preferably 0.7 to 10 MPa, and particularly preferably 1 to 8 MPa. The temperature of the solution in the dissolution tank is preferably 3 to 140° C., more preferably 5 to 120° C., and particularly preferably 10 to 100° C.

(5) Solid-Liquid Separation Step

The insolubles in the solution from the dissolution step are partly or completely removed by the solid-liquid separation. The solid-liquid separation is conducted by a known method such as filtration, centrifugal separation and sediment separation, preferably by filtration and more preferably by filtration using a sintered metal filter or a strainer because of easy operation. The filtration may be conducted with a filtering aid.

The insolubles to be removed in the solid-liquid separation step contain dicyanobenzene polymers such as dicyanobenzene trimers. The dicyanobenzene trimers include linear compounds and cyclic compounds having a triazine ring, for example, phthalonitrile trimers such as 2,4,6-tris(2-cyanophenyl)-1,3,5-triazine (Formula 1), 2,4,6-tris(3-cyanophenyl-1,3,5-triazine (Formula 2), and 2,4,6-tris(4-cyanophenyl)-1,3,5-triazine (Formula 3). The dicyanobenzene polymers other than dicyanobenzene trimers include an isophthalonitrile pentamer represented by the following formula 4.

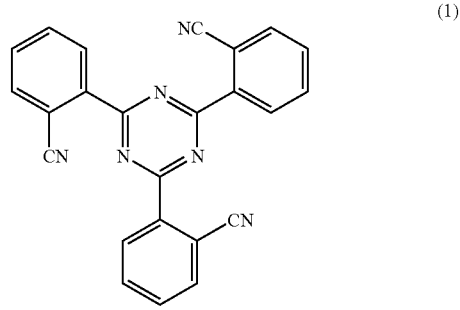

(1)

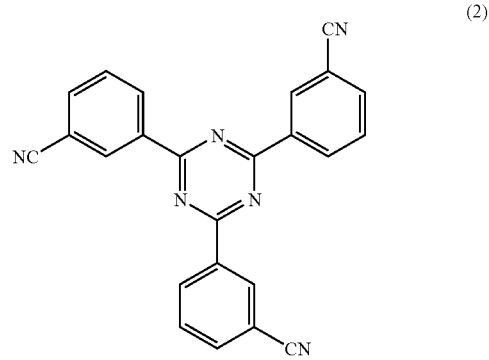

(2)

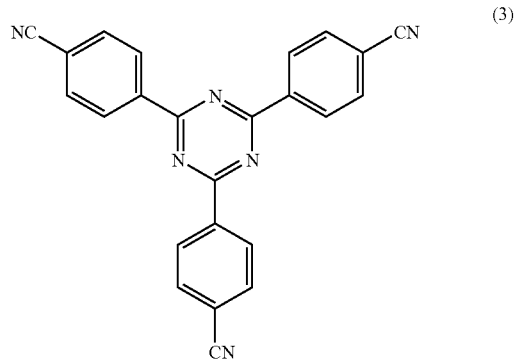

(3)

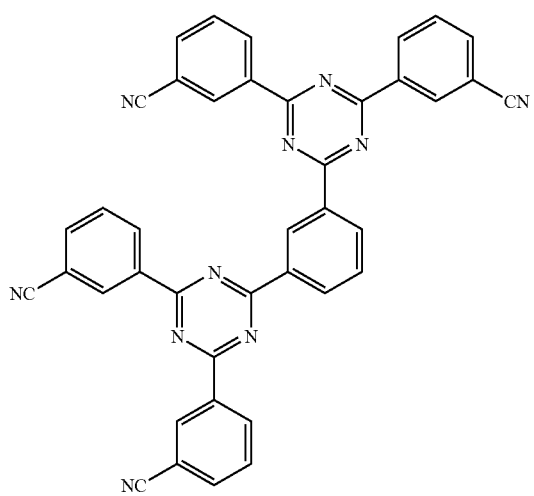

(4)

By reducing the content of the dicyanobenzene polymers in the solid-liquid separation step, the deactivation of the hydrogenation catalyst is prevented. To prolong the life time of the hydrogenation catalyst, the content of the dicyanobenzene polymers in dicyanobenzene to be subjected to the hydrogenation is preferably 0.1% by weight or less.

(6) Hydrogenation Step

The filtrate from the solid-liquid separation step is fed to the hydrogenation reactor and dicyanobenzene is hydrogenated therein in liquid phase in the presence of a catalyst. Although the filtrate from the solid-liquid separation step already contains the solvent added in the dissolution step, various solvents stable under the hydrogenation reaction conditions may be freshly added. Examples of such solvents include aromatic hydrocarbon solvents such as toluene, xylene and trimethylbenzene; ether solvents such as tetrahydrofuran and dioxane; alcohol solvents such as methanol, ethanol and propanol; aromatic monoamine solvents such as benzylamine and methylbenzylamine; lower aliphatic amide solvents such as dimethylformamide and dimethylacetamide; and liquid ammonia. These solvents may be used in combination of two or more. A higher concentration of liquid ammonia, for example, 60% by weight or more (inclusive of 100% by weight) is preferred, because the higher the concentration of liquid ammonia in the solvent, the higher the yield of the hydrogenation. The amount of the solvent in the hydrogenation is preferably 1 to 99 parts by weight, more preferably 3 to 99 parts by weight, and particularly preferably 5 to 99 parts by weight, each based on one part by weight of dicyanobenzene. Within the above ranges, the production method is economically advantageous because the energy for recovering the solvents is saved and the selectivity of xylylenediamine in the hydrogenation is good.

Hydrogen used in the hydrogenation may contain impurities inert to the hydrogenation, for example, methane, nitrogen, etc. However, if the concentration of impurities is high, the total pressure for the hydrogenation should be increased so as to attain a necessary hydrogen partial pressure, thereby making the method industrially disadvantageous. Therefore, the concentration of hydrogen is preferably 50 mol % or more.

The hydrogenation catalyst may be known supported metal catalysts, non-supported metal catalysts, Raney catalysts, or noble metal catalysts, with nickel- and/or cobalt-containing catalysts being particularly preferred. The hydrogenation catalyst may be used in an amount used in a known hydrogenation of dicyanobenzene in liquid phase and not particularly limited in the present invention.

The hydrogenation may be carried out by either a fixed bed method or a slurry bed method, and either a batch-wise manner or a continuous manner. In the fixed bed, continuous flow method, a circulation method in which part of the hydrogenation product solution from the hydrogenation reactor is continuously circulated to the hydrogenation reactor may be possible. The hydrogenation may be also carried out by the circulation method alone or in combination of the circulation method with one pass method as described in JP 2008-31155A. In the batch-wise hydrogenation, the hydrogenation time is preferably 0.5 to 8 h. In the continuous hydrogenation, the space velocity (LHSV: liquid hourly space velocity) of the raw material is preferably 0.1 to 10 $h^{-1}$.

The pressure and temperature of the hydrogenation are selected so as to maintain the solvent in liquid phase. The temperature is preferably 20 to 200° C., more preferably 30 to 150° C., and particularly preferably 40 to 120° C. The hydrogen pressure is preferably 1 to 30 MPa, more preferably 2 to 25 MPa, and particularly preferably 3 to 20 MPa.

It is necessary to expedite the progress of the hydrogenation of nitrile groups to aminomethyl groups for the efficient production of xylylenediamine by the hydrogenation of dicyanobenzene, and it is preferred to select the reaction conditions capable of keeping the concentrations of dicyanobenzene and cyanobenzylamine in the hydrogenation product solution low. For example, it is recommended to keep the amount of cyanobenzylamine in the hydrogenation product solution at preferably 1.0% or less, more preferably 0.5% or less, and particularly preferably 0.2% or less, each based on the amount of xylylenediamine. In addition, the conversion of dicyanobenzene is preferably 99.50% or more, more preferably 99.90% or more, and particularly preferably 99.95% or more. The progress of the hydrogenation can be kept as described above by suitably selecting the temperature or reaction time while combining the reaction conditions such as solvents, catalysts, raw materials, hydrogen pressure and reaction manner mentioned above.

The xylylenediamine produced by the hydrogenation may be purified by a known method such as distillation. If xylylenediamine with a higher purity is intended, cyanobenzylamine in xylylenediamine should be removed. Since the difference in the boiling points of cyanobenzylamine and the corresponding xylylenediamine is generally small, the separation of these compounds by usual distillation is difficult. Therefore, cyanobenzylamine may be removed by a method other than distillation before the purification by distillation. The removal of cyanobenzylamine is effected, for example, by a method in which cyanobenzylamine is hydrated to cyanobenzamide which is relatively easy-to-separate from xylylenediamine by distillation or by a method described in JP 2007-332135A in which liquid ammonia used as the hydrogenation solvent is distilled off and then cyanobenzylamine is catalytically hydrogenated in the presence of a catalyst thereby to reduce the amount of the cyanobenzylamine. although not particularly limited thereto.

EXAMPLES

The present invention will be described in more detail with reference to the following examples. However, it should be noted that the scope of the present invention is not limited thereto. The compositional analysis of dicyanobenzene (inclusive of dicyanobenzene trimers) was made by liquid chromatography. Gas chromatography was used for the compositional analysis of the hydrogenation product solution.

(1) Liquid Chromatography

The analysis was made by a high-pressure gradient LC system with

UV-VIS detector manufactured by Shimadzu Corporation using LC column manufactured by Shiseido Co., Ltd. A mixture of acetonitrile (manufactured by Wako Pure Chemical Industries, Ltd., special grade) and a 0.5% by weight aqueous solution of phosphoric acid was used as the solvent and mobile phase.

(2) Gas Chromatography

The analysis was made by a 6890-type GC analysis system manufactured by Agilent Technologies, Inc. equipped with DB-1 GC column manufactured by J&W Scientific Inc. The inlet temperature was 230° C., the detector temperature was 295° C., and the column oven temperature was raised from 100° C. to 280° C. (maintained at 100° C. for 10 min and then raised at a rate of 5° C/min). The sample for GC analysis was prepared by sampling a 2-mL solution from the solution before hydrogenation or after hydrogenation, removing ammonia (product of Mitsubishi Gas Chemical Company, Inc.) from the sampled solution by heating, adding 0.1 g of diphenylmethane (manufactured by Wako Pure Chemical Industries, Ltd., special grade) to the resulting residue as the internal standard, and dissolving the resulting mixture in 10 g of methanol or dioxane (each manufactured by Wako Pure Chemical Industries, Ltd., special grade).

Example 1

(1) Ammoxidation Step
Preparation of Ammoxidation Catalyst

To 229 g of vanadium pentoxide (manufactured by Wako Pure Chemical Industries, Ltd., special grade), 500 mL of water (distilled water) was added and then 477 g of oxalic acid (manufactured by Wako Pure Chemical Industries, Ltd., special grade) was dissolved in the resulting solution at 80 to 90° C. under heating and stirring, to obtain a vanadium oxalate solution. Separately, to 963 g of oxalic acid, 400 mL of water was added and heated to 50 to 60° C., and then, an aqueous solution of 252 g of chromic anhydride (manufactured by Wako Pure Chemical Industries, Ltd., special grade) in 200 mL of water was dissolved under vigorous stirring, to obtain a chromium oxalate solution. The vanadium oxalate solution was mixed with the chromium oxalate solution at 50 to 60° C. to obtain a vanadium-chromium solution. To the vanadium-chromium solution, an aqueous solution of 41.1 g of phosphorus molybdate ($H_3(PMo_{12}O_{40})\cdot 20H_2O$ (manufactured by Nippon Inorganic Colour & Chemical Co., Ltd.) in 100 mL of water and further an aqueous solution of 4.0 g of potassium acetate (manufactured by Wako Pure Chemical Industries, Ltd., special grade) in 100 mL of water were added. Thereafter, 2500 g of a 20% by weight aqueous silica sol ($Na_2O$ content: 0.02% by weight) was added. To the resulting slurry, 78 g of boric acid was added and well mixed and then the slurry was condensed by heating to about 3800 g. The resulting catalyst solution was spray-dried in a drier while maintaining the inlet at 250° C. and the outlet at 130° C. After further drying at 130° C. in a dryer for 12 h, the dried catalyst was burnt at 400° C. for 0.5 h and then burnt at 550° C. for 8 h in air flow. The atomic ratio of the obtained catalyst was V:Cr:B:Mo:P:Na:K=1:1:0.5:0.086:0.007:0.009:0.020 and the catalyst concentration was 50% by weight.

(1) Ammoxidation Step

The following steps were carried out in accordance with the flow chart shown in FIG. 1. An ammoxidation reactor A was packed with 6 L of the flowable catalyst prepared above. After preheating to 350° C., a mixture of air, m-xylene (product of Mitsubishi Gas Chemical Company, Inc., hereinafter referred to as "MX") and ammonia (product of Mitsubishi Gas Chemical Company, Inc.) was fed to the reactor. The feeding amount of MX was 350 g/h, the ammonia/MX molar ratio was 11, the oxygen/MX molar ratio was 5.4, and the space velocity SV was $630\ h^{-1}$. The reaction temperature was 420° C. and the reaction pressure was 0.2 MPa.

(2) Absorption Step

The reaction product gas from the top portion of the ammoxidation reactor A was introduced to an isophthalonitrile absorption column B, where isophthalonitrile in the reaction product gas was allowed to be absorbed into m-tolunitrile solvent (product of Mitsubishi Gas Chemical Company, Inc.). The isophthalonitrile absorption column B was made of SUS304 and had a condenser at its upper portion. The barrel portion thereof had a 100-mm inner diameter and a 800-mm height. The lower portion (450 mm) of the barrel portion was made into a double-walled structure for steam heating. A gas inlet was disposed at the bottom portion of the column. Into the absorption column 2 kg of m-tolunitrile was charged and the temperature was raised to 175° C. Then, the ammoxidation product gas was contacted with m-tolunitrile for 2 h. The solution just after the absorbing operation contained 74% by weight of m-tolunitrile and 25% by weight of isophthalonitrile.

(3) Removal Step of Low-Boiling Compounds

The isophthalonitrile-containing solution was fed to the middle portion of a distillation column C for separating low-boiling compounds. The distillation was carried out at a column top pressure of 6 kPa, a column top temperature of 120° C., and a column bottom temperature of 183° C. The residence time at the column bottom was 60 min or 180 min. The molten isophthalonitrile was drawn from the column bottom while distilling off m-tolunitrile and other low-boiling compounds from the column top. The purity of the obtained molten isophthalonitrile is shown in Table 1.

TABLE 1

Purity of molten isophthalonitrile

| | Residence time (at column bottom) | |
|---|---|---|
| Composition (% by weight) | 60 min | 180 min |
| isophthalonitrile | 96.38 | 96.31 |
| isophthalonitrile trimer* | 0.12 | 0.16 |
| m-tolunitrile | 0.11 | 0.11 |
| 3-cyanobenzamide | 1.29 | 1.38 |
| 3-cyanobenzoic acid | 0.20 | 0.12 |
| others | 1.90 | 1.92 | isophthalonitrile trimer: 2,4,6-tris(3-cyanophenyl)-1,3,5-triazine (4) Dissolution Step The obtained molten isophthalonitrile (residence time at bottom of distillation column: 60 min) was fed to a dissolution tank D (made of SUS304 having a volume of 1 L) from its side portion at a flow rate of 280 g/h and liquid ammonia was fed to the dissolution tank D from its upper portion at a flow rate of 5320 g/h, thereby dissolving isophthalonitrile in liquid ammonia at 2 MPa and 25° C.

(5) Solid-Liquid Separation Step

Then, a solution containing insolubles was drawn from the bottom of the dissolution tank D and filtered through a filter E (stainless strainer with a pore size of 40 μm) while transferring the solution by pressure difference. By removing 0.17 g of 2,4,6-tris(3-cyanophenyl)-1,3,5-triazine as part of the filtered-off product per one hour, a filtrate was obtained at a rate of 279.8 g/h. The composition of the crude isophthalonitrile obtained by removing liquid ammonia from the filtrate is shown in Table 2. Upon comparing with the results in Table 1, it can be found that the content of 2,4,6-tris(3-cyanophenyl)-1,3,5-triazine is drastically reduced.

(6) Hydrogenation Step

In a tubular vertical hydrogenation reactor F (made of SUS304 having an inner diameter of 100 mm), 4 L of a commercially available nickel/diatomaceous earth supported catalyst with a nickel content of 50% by weight (columnar shape with a diameter of 5 mm and a height of 5 mm) was packed. Then, the catalyst was reduced under hydrogen flow at 200° C. for activation. After cooling, hydrogen gas was introduced into the reactor under pressure to maintain the pressure constant at 10 MPa, and the catalyst layer was maintained at 90° C. by external heating. The filtrate obtained in the solid-liquid separation step was continuously fed to the reactor from its upper portion at a rate of 5.60 kg/h while flowing hydrogen gas from the upper portion of the reactor at a flow rate of 265 NL/h. The amount of the 3-cyanobenzylamine (reaction intermediate) increased with time. The reaction results and the total feeding amount of isophthalonitrile to the reactor at the time when the amount of 3-cyanobenzylamine in the hydrogenation product solution reached 0.10% by weight of the amount of m-xylylenediamine are shown in Table 3.

After removing liquid ammonia from the hydrogenation product solution by a simple distillation, the remaining ammonia was further removed by bubbling nitrogen gas. The reaction product solution after removing ammonia was catalytically hydrogenated again in the present of a commercially available nickel/diatomaceous earth supported catalyst with a nickel content of 50% by weight in a fixed bed manner (WHSV (weight hourly space velocity: 0.5 h$^{-1}$, reaction temperature: 80° C., reaction pressure: 2 MPa), to obtain crude m-xylylenediamine. The crude m-xylylenediamine was distilled under reduced pressure of 6 kPa using a distillation column with 10 theoretical plates, to obtain a purified m-xylylenediamine with 99.99% purity. The content of 3-cyanobenzylamine in the obtained m-xylylenediamine was 0.001% by weight or less.

Example 2

The procedure of Example 1 was repeated up to the dissolution step except for using the molten isophthalonitrile (residence time at the bottom of distillation column: 180 min). By removing 0.20 g of 2,4,6-tris(3-cyanophenyl)-1,3,5-triazine as part of the filtered-off product per one hour, a filtrate was obtained at a rate of 279.7 g/h. The composition of the crude isophthalonitrile obtained by removing liquid ammonia from the filtrate is shown in Table 2.

The obtained isophthalonitrile was hydrogenated in the same manner as in Example 1 except for using the filtrate obtained in the above filtration. The reaction results and the total feeding amount of isophthalonitrile to the reactor at the time when the amount of 3-cyanobenzylamine in the hydrogenation product solution reached 0.10% by weight of the amount of m-xylylenediamine are shown in Table 3.

Comparative Examples 1

A raw solution for hydrogenation was prepared by mixing 5.0% by weight of the molten isophthalonitrile (residence time at the bottom of distillation column: 60 min) obtained in Example 1 and 95% by weight of liquid ammonia. The hydrogenation was conducted in the same manner as in Example 1 except for using the obtained raw solution for hydrogenation in place of the filtrate obtained in the solid-liquid separation step. The composition of the crude isophthalonitrile obtained by removing liquid ammonia from the raw solution for hydrogenation is shown in Table 2. The reaction results and the total feeding amount of isophthalonitrile to the reactor at the time when the amount of 3-cyanobenzylamine in the hydrogenation product solution reached 0.10% by weight of the amount of m-xylylenediamine are shown in Table 3. The hydrogenation was further continued, and the reaction results at the time when the total feeding amount of isophthalonitrile reached 26.3 kg were isophthalonitrile conversion of 99.93%, m-xylylenediamine selectivity of 88.03 mol %, and 3-cyanobenzylamine selectivity of 2.34 mol %.

Comparative Examples 2

The hydrogenation of isophthalonitrile was conducted in the same manner as in Comparative Example 1 except for using the molten isophthalonitrile (residence time at the bottom of distillation column: 180 min) obtained in Example 1 in place of the molten isophthalonitrile (residence time at the bottom of distillation column: 60 min). The composition of the crude isophthalonitrile obtained by removing liquid ammonia from the raw solution for hydrogenation is shown in Table 2. The reaction results and the total feeding amount of isophthalonitrile to the reactor at the time when the amount of 3-cyanobenzylamine in the hydrogenation product solution reached 0.10% by weight of the amount of m-xylylenediamine are shown in Table 3. The hydrogenation was further continued, and the reaction results at the time when the total feeding amount of isophthalonitrile reached 23.9 kg were isophthalonitrile conversion of 98.48%, m-xylylenediamine selectivity of 71.59 mol %, 3-cyanobenzylamine selectivity of 9.89 mol %.

Example 3

The procedure of Example 1 was repeated up to the dissolution step except for using an MX/liquid ammonia mixed solvent (MX: 20% by weight, liquid ammonia: 80% by weight) in place of liquid ammonia solvent and feeding the mixed solvent to the dissolution tank D at a rate of 6650 g/h. By removing 0.16 g of 2,4,6-tris(3-cyanophenyl)-1,3,5-triazine as part of the filtered-off product per one hour, a filtrate was obtained at a rate of 279.8 g/h. The composition of the crude isophthalonitrile obtained by removing MX and liquid ammonia from the filtrate is shown in Table 2.

The hydrogenation of isophthalonitrile was conducted in the same manner as in Example 1 except for continuously feeding the filtrate obtained in the above filtration to the reactor from its upper portion at a rate of 6.93 kg/h. The reaction results and the total feeding amount of isophthalonitrile to the reactor at the time when the amount of 3-cyanobenzylamine in the hydrogenation product solution reached 0.10% by weight of the amount of m-xylylenediamine are shown in Table 3.

Comparative Examples 3

A raw solution for hydrogenation was prepared by mixing 4.04% by weight of the molten isophthalonitrile (residence time at the bottom of distillation column: 60 min) and 95.96% by weight of an MX/liquid ammonia mixed solvent (MX: 20% by weight, liquid ammonia: 80% by weight). The hydrogenation of isophthalonitrile was conducted in the same manner as in Example 3 except for continuously feeding the obtained raw solution for hydrogenation to the reactor from its upper portion at a rate of 6.93 kg/h. The composition of the crude isophthalonitrile obtained by removing the mixed solvent from the raw solution for hydrogenation is shown in Table 2. The reaction results and the total feeding amount of isophthalonitrile to the reactor at the time when the amount of 3-cyanobenzylamine in the hydrogenation product solution reached 0.10% by weight of the amount of m-xylylenediamine are shown in Table 3. The hydrogenation was further continued, and the reaction results at the time when the total feeding amount of isophthalonitrile reached 26.2 kg were isophthalonitrile conversion of 99.94%, m-xylylenediamine selectivity of 88.88 mol %, and 3-cyanobenzylamine selectivity of 2.11 mol %.

TABLE 2

| Composition (% by weight) | Examples | | | Comparative Examples | | |
|---|---|---|---|---|---|---|
| | 1 | 2 | 3 | 1 | 2 | 3 |
| isophthalonitrile | 96.46 | 96.41 | 96.46 | 96.38 | 96.31 | 96.38 |
| isophthalonitrile trimer* | 0.0580 | 0.0880 | 0.0621 | 0.1200 | 0.1600 | 0.1200 |
| m-tolunitrile | 0.11 | 0.11 | 0.11 | 0.11 | 0.11 | 0.11 |
| 3-cyanobenzamide | 1.29 | 1.38 | 1.29 | 1.29 | 1.38 | 1.29 |
| 3-cyanobenzoic acid | 0.20 | 0.12 | 0.20 | 0.20 | 0.12 | 0.20 |
| others | 1.88 | 1.89 | 1.88 | 1.90 | 1.92 | 1.90 | isophthalonitrile trimer: 2,4,6-tris(3-cyanophenyl)-1,3,5-triazine

TABLE 3

| Results of reaction (mol %) | Examples | | | Comparative Examples | | |
|---|---|---|---|---|---|---|
| | 1 | 2 | 3 | 1 | 2 | 3 |
| Conversion of isophthalonitrile | 99.99 | 99.99 | 99.99 | 99.99 | 99.99 | 99.99 |
| Selectivity of m-xylylenediamine | 94.90 | 94.70 | 94.80 | 94.20 | 93.70 | 94.50 |
| Selectivity of 3-cyanobenzylamine | 0.09 | 0.09 | 0.09 | 0.09 | 0.09 | 0.09 |
| Total feeding amount (kg) | 26.3 | 23.9 | 26.2 | 14.8 | 11.2 | 15.3 |

What is claimed is:

1. A method of producing xylylenediamine which comprises the following steps:
   (1) an ammoxidation step of ammoxidizing xylene by a vapor phase catalytic reaction with ammonia and an oxygen-containing gas in the presence of a catalyst, thereby producing an ammoxidation gas containing dicyanobenzene;
   (2) an absorption step of contacting the ammoxidation gas with an organic solvent directly, thereby absorbing dicyanobenzene in the organic solvent;
   (3) a removal step of low-boiling compounds wherein the dicyanobenzene-containing solution from the absorption step is distilled, to remove compounds having a boiling point lower than that of dicyanobenzene together with the organic solvent partly or completely and obtain a molten dicyanobenzene;
   (4) a dissolution step of dissolving the molten dicyanobenzene from the removal step of low-boiling compounds in a liquid ammonia solvent or a mixed solvent of at least one aromatic hydrocarbon and liquid ammonia;
   (5) a solid-liquid separation step of removing insolubles in the solution from the dissolution step partly or completely; and
   (6) a hydrogenation step of hydrogenating dicyanobenzene in the solution from the solid-liquid separation step in liquid phase in the presence of a catalyst.

2. The method according to claim 1, wherein the insolubles removed in the solid-liquid separation step (5) comprises dicyanobenzene polymers.

3. The method according to claim 1, wherein the solution from the solid-liquid separation step (5) contains dicyanobenzene polymers in an amount of 0.1% by weight or less of dicyanobenzene.

4. The method according to claim 1, wherein the insolubles in the solution from the dissolution step (4) is removed by filtration in the solid-liquid separation step (5).

5. The method according to claim 1, wherein xylene is m-xylene and dicyanobenzene is isophthalonitrile.

6. The method according to claim 2, wherein the dicyanobenzene polymers are dicyanobenzene trimers having a triazine ring.

7. The method according to claim 1, wherein the catalyst used in the ammoxidation step (1) is a vanadium- and/or chromium-containing catalyst.

8. The method according to claim 1, wherein the organic solvent for absorbing dicyanobenzene in the absorption step (2) is at least one organic solvent selected from the group consisting of alkylbenzenes, heterocyclic compounds, aromatic nitriles and heterocyclic nitriles.

9. The method according to claim 1, wherein the hydrogenation in the hydrogenation step (6) is conducted after freshly adding a liquid ammonia solvent or a mixed solvent of at least one aromatic hydrocarbon and liquid ammonia to the solution from the solid-liquid separation step (5).

10. The method according to claim 1, wherein a concentration of liquid ammonia in the mixed solvent used in the dissolution step (4) is 30% by weight or more.

11. The method according to claim 1, wherein the hydrogenation of dicyanobenzene in the hydrogenation step (6) is carried out in a fixed bed reactor.

12. The method according to claim 1, wherein the hydrogenation catalyst used in the hydrogenation step (6) is a nickel- and/or cobalt-containing catalyst.

13. The method according to claim 1, wherein the hydrogenation catalyst used in the hydrogenation step (6) is a nickel-containing catalyst.

* * * * *